(12) United States Patent
Gorsline et al.

(10) Patent No.: US 9,931,146 B2
(45) Date of Patent: Apr. 3, 2018

(54) SYSTEMS, METHODS, AND APPARATUSES FOR FUSION, STABILIZATION, OR FIXATION OF BONES

(71) Applicants: Robert Gorsline, Columbus, OH (US); Jonathan Feibel, Columbus, OH (US)

(72) Inventors: Robert Gorsline, Columbus, OH (US); Jonathan Feibel, Columbus, OH (US); Nicholas J. Vallo, New Albany, OH (US); Christos Ragais, New Albany, OH (US); Christopher Brown, Columbus, OH (US); Christopher Hawker, Columbus, OH (US); Jeffrey J. Root, Columbus, OH (US)

(73) Assignees: Jonathan Feibel, Columbus, OH (US); Robert Gorsline, Columbus, OH (US)

(*) Notice: Subject to any disclaimer, the term of this patent is extended or adjusted under 35 U.S.C. 154(b) by 0 days.

(21) Appl. No.: 15/168,181

(22) Filed: May 30, 2016

(65) Prior Publication Data

US 2016/0270828 A1 Sep. 22, 2016

Related U.S. Application Data

(63) Continuation of application No. 14/175,968, filed on Feb. 7, 2014, now Pat. No. 9,351,771.

(60) Provisional application No. 61/912,543, filed on Dec. 5, 2013, provisional application No. 61/762,462, filed on Feb. 8, 2013.

(51) Int. Cl.
*A61B 17/72* (2006.01)
*A61B 17/88* (2006.01)
*A61B 17/17* (2006.01)

(52) U.S. Cl.
CPC ...... *A61B 17/7225* (2013.01); *A61B 17/7233* (2013.01); *A61B 17/7291* (2013.01); *A61B 17/8869* (2013.01); *A61B 17/1725* (2013.01)

(58) Field of Classification Search
CPC ............ A61B 17/7225; A61B 17/7233; A61B 17/725; A61B 17/7241; A61B 17/842; A61B 17/72; A61B 17/7216
See application file for complete search history.

(56) References Cited

U.S. PATENT DOCUMENTS

| | | | | |
|---|---|---|---|---|
| 4,190,044 | A * | 2/1980 | Wood | A61B 17/72 606/63 |
| 5,034,012 | A * | 7/1991 | Frigg | A61B 17/72 606/104 |
| 6,120,504 | A * | 9/2000 | Brumback | A61B 17/72 606/62 |
| 6,231,576 | B1 * | 5/2001 | Frigg | A61B 17/7208 606/60 |
| 2007/0213725 | A1 * | 9/2007 | Hack | A61B 17/7225 606/62 |

* cited by examiner

*Primary Examiner* — Julianna N Harvey
(74) *Attorney, Agent, or Firm* — Benesch Friedlander Coplan & Aronoff, LLP; Benjamen E. Kern; Stephen D. Scanlon

(57) ABSTRACT

Systems, methods, and apparatuses for fusion, stabilization, or fixation of bones are provided.

30 Claims, 12 Drawing Sheets

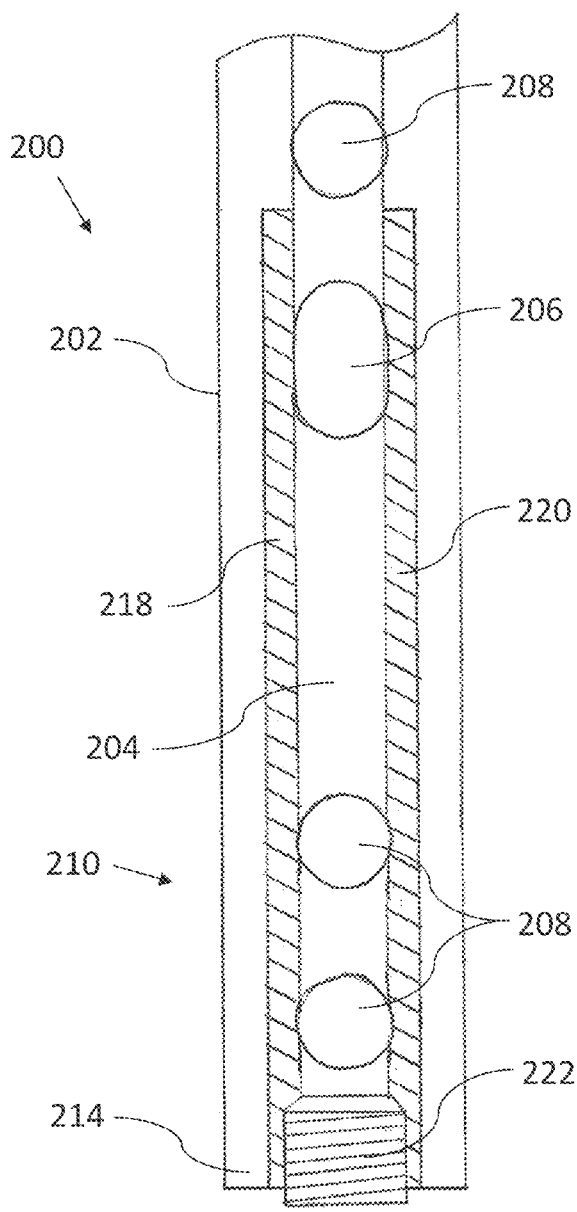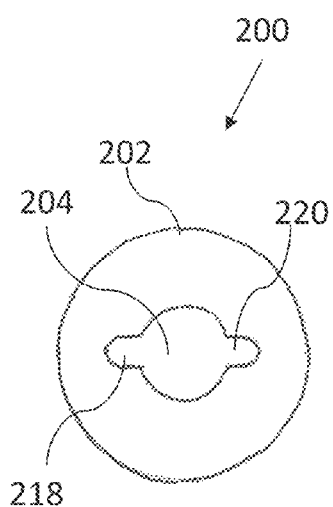
FIG. 2
FIG. 3

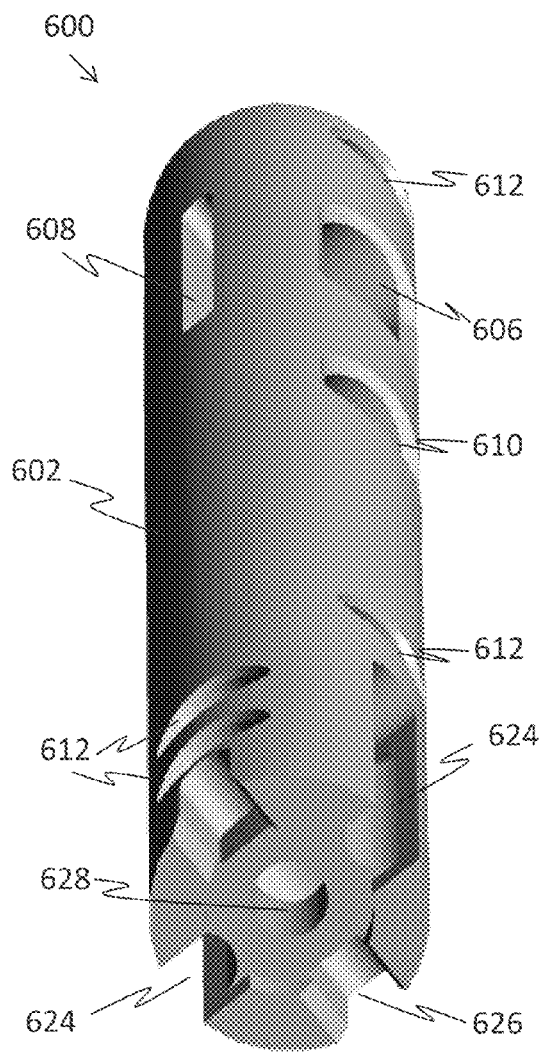
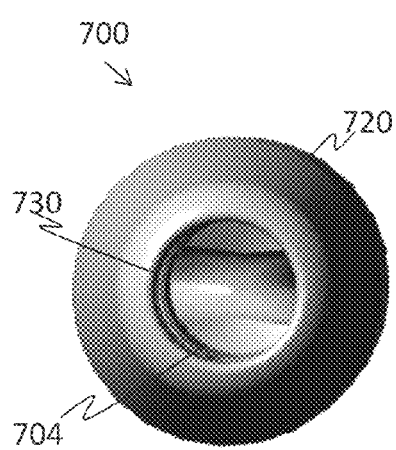
FIG. 6
FIG. 7

SYSTEMS, METHODS, AND APPARATUSES FOR FUSION, STABILIZATION, OR FIXATION OF BONES

CROSS-REFERENCE TO RELATED APPLICATIONS

This application claims priority to U.S. Pat. No. 9,351,771, issued on May 31, 2016, which claims priority to U.S. Provisional Patent Application No. 61/762,462, filed on Feb. 8, 2013, and U.S. Provisional Patent Application No. 61/912,543, filed on Dec. 5, 2013, each of which is incorporated by reference herein in its entirety.

BACKGROUND

The implantation, use, and tensioning of orthopedic implanted devices for fusion, stabilization, and fixation of joints, fractures, and other fusions may involve various complicated processes and components. Many of these devices may use invasive exterior tensioning devices, which may provide little control of tension and/or inaccurate means of measuring tension.

The present application appreciates that devising orthopedic systems, methods, and apparatuses for fusion, stabilization, or fixation of bones may be a challenging endeavor.

SUMMARY

In one embodiment, an apparatus for causing compression between bone elements is provided, the apparatus comprising: an elongated shaft comprising an longitudinal inner bore and at least one compression slot; at least one channel oriented longitudinally along at least a portion of the longitudinal inner bore, wherein the at least one channel is in communication with the at least one compression slot.

In another embodiment, an apparatus for causing compression between bone elements is provided, the apparatus comprising: an elongated shaft comprising an longitudinal inner bore, at least one compression slot, a proximal end, and a distal end; a first channel oriented longitudinally along at least a portion of the longitudinal inner bore on a first side of the longitudinal inner bore and in communication with the proximal end of the elongated shaft; a second channel oriented longitudinally along at least a portion of the longitudinal inner bore on a second side of the longitudinal inner bore and in communication with the proximal end of the elongated shaft, wherein the first side of the longitudinal inner bore and the second side of the longitudinal inner bore are substantially opposed; and a tensioning cable extending from the proximal end of the elongated shaft, through the first channel, about a portion of the at least one compression slot, and through the second channel to the proximal end of the elongated shaft.

In another embodiment, an apparatus for causing compression between bone elements is provided. The apparatus may include an elongated shaft. The elongated shaft may include a longitudinal inner bore. The apparatus may include at least one compression slot. The at least one compression slot may be in communication with the longitudinal inner bore. The apparatus may include at least one tensioning cable clearance slot. The at least one tensioning cable clearance slot may be offset from the at least one compression slot. The apparatus may include at least one fixation aperture.

In another embodiment, an apparatus for causing compression between bone elements is provided. The apparatus may include an elongated shaft. The elongated shaft may include a longitudinal inner bore. The apparatus may include at least one compression slot. The at least one compression slot may be located on the elongated shaft and may be in communication with the longitudinal inner bore. The apparatus may include at least one tensioning cable clearance slot. The at least one tensioning cable clearance may be located on the elongated shaft and may be substantially orthogonally offset from the at least one compression slot. The at least one tensioning cable clearance slot may be in communication with the longitudinal inner bore. The at least one tensioning cable clearance slot may be operable to allow a tensioning cable to bow radially outward from the longitudinal inner bore to prevent the tensioning cable from interfering with an insertion of a transverse bolt into the at least one compression slot. The apparatus may include at least one dynamization slot. The at least one dynamization slot may be in communication with the longitudinal inner bore. The apparatus may include at least one fixation aperture. The at least one fixation aperture may be operable to provide static fixation of the elongated shaft to the bone elements. The apparatus may include at least one tensioning cable aperture. The at least one tensioning cable aperture may be in communication with the longitudinal inner bore. The at least one tensioning cable aperture may provide one of an ingress into the longitudinal inner bore and an egress out of the longitudinal inner bore for at least one tensioning cable end. The at least one tensioning cable aperture may be in communication with an external tensioning cable guide channel. The apparatus may include an external tensioning cable guide channel. The external tensioning cable channel may be on an external surface of the elongated shaft. The external tensioning cable guide channel may be in communication with the at least one tensioning cable aperture and may be operable to guide a tensioning cable.

In one embodiment, a system for causing compression between bone elements is provided, the system comprising: an apparatus for causing compression between bone elements, comprising: an elongated shaft comprising a longitudinal inner bore; at least one compression slot, the at least one compression slot in communication with the longitudinal inner bore, and the at least one compression slot accepting at least one transverse bolt; at least one tensioning cable clearance slot, the at least one tensioning cable clearance slot offset from the at least one compression slot; and at least one fixation aperture; a tensioning cable operatively connected to the at least one transverse bolt; and a tensioning device configured apply a tension to the tensioning cable.

In another embodiment, a system for causing compression between bone elements is provided, the system comprising: an elongated shaft comprising an longitudinal inner bore, at least one compression slot, a proximal end, and a distal end, wherein a first transverse bolt extends through the at least one compression slot; a first channel oriented longitudinally along at least a portion of the longitudinal inner bore on a first side of the longitudinal inner bore and in communication with the proximal end of the elongated shaft; a second channel oriented longitudinally along at least a portion of the longitudinal inner bore on a second side of the longitudinal inner bore and in communication with the proximal end of the elongated shaft, a tensioning cable extending from the proximal end of the elongated shaft, through the first channel, about a portion of the first transverse bolt, and through the second channel to the proximal end of the elongated shaft; and a tensioning device configured to impart tension upon the tensioning cable.

In another embodiment, a system for causing compression between bone elements is provided. The system may include an apparatus for causing compression between bone elements. The apparatus may further include at least one interface operable to connect the apparatus to the system. The apparatus may also include a targeting arm. The apparatus may also include a soft tissue protection sleeve. The apparatus may also include a tensioning device.

BRIEF DESCRIPTION OF THE DRAWINGS

The accompanying figures, which are incorporated in and constitute a part of the specification, illustrate various example apparatuses and systems, and are used merely to illustrate various example embodiments.

FIG. 2 is a longitudinal-sectional view of an example arrangement of an apparatus for causing compression between bone elements.

FIG. 3 is a cross-sectional view of an example arrangement of an apparatus for causing compression between bone elements.

FIG. 6 is a perspective view of a proximal end of an example arrangement of an apparatus for causing compression between bone elements.

FIG. 7 is a perspective view of a distal end of an example arrangement of an apparatus for causing compression between bone elements.

DETAILED DESCRIPTION

Figure 1:
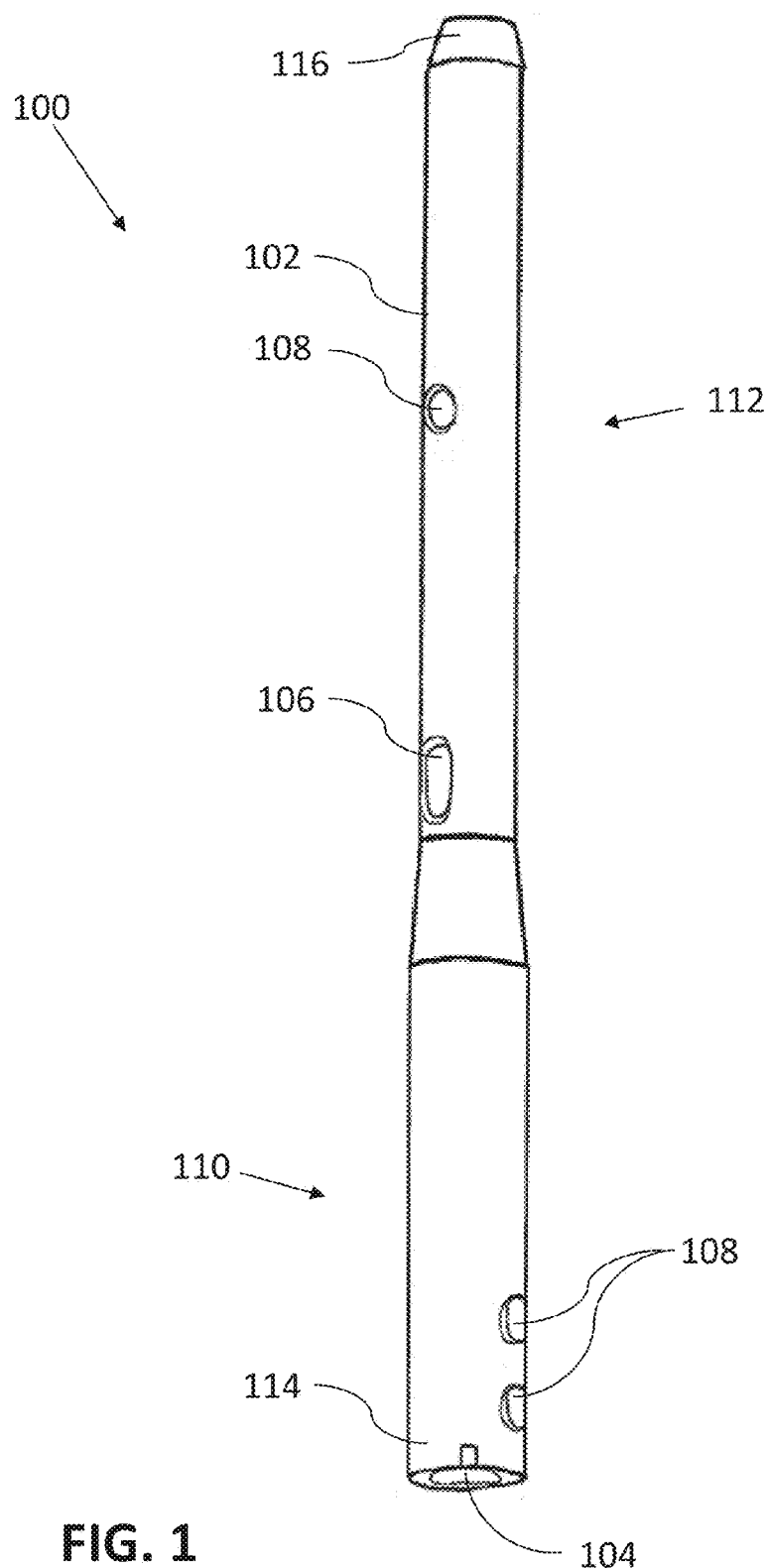
FIG. 1 is a perspective view of an example arrangement of an apparatus for causing compression between bone elements.

FIG. 1 illustrates a perspective view of an example arrangement of an apparatus 100 for causing compression between bone elements. Apparatus 100 comprises an elongated shaft 102 having a longitudinal inner bore 104 extending longitudinally through at least a portion of elongated shaft 102. The term longitudinal bore may be used interchangeably with longitudinal bore herein.

Elongated shaft 102 comprises at least one compression slot 106 extending partially or completely across elongated shaft 102. Compression slot 106 may be configured to accept a transverse bolt (not shown), which may extend across at least a portion of elongated shaft 102. The transverse bolt may be configured to connect to a bone element. Compression slot 106 may be an oblong transverse aperture.

In one embodiment, elongated shaft 102 comprises at least one static fixation aperture 108 extending partially or complete across elongated shaft 102. In another embodiment, elongated shaft 102 comprises a plurality of static fixation apertures 108. Static fixation aperture 108 may be configured to accept a transverse bolt (not shown), which may extend across at least a portion of elongated shaft 102. The transverse bolt may be configured to connect to a bone element. Static fixation aperture 108 may be a circular transverse aperture.

In one embodiment, the transverse bolt may comprise any of a temporary or permanent bolt, screw, or pin. In another embodiment, the transverse bolt may comprise a locking screw. In another embodiment, the transverse bolt may comprise any fastening device capable of joining elongated shaft 102 to a bone element.

In one embodiment, elongated shaft 102 comprises a proximal portion 110 and a distal portion 112. In one embodiment, proximal portion 110 comprises a greater diameter than distal portion 112. In another embodiment, proximal portion 110 comprises a diameter substantially the same as distal portion 112. In another embodiment, proximal portion 110 comprises a lesser diameter than distal portion 112. In one embodiment, the junction between proximal portion 110 and distal portion 112 may be tapered.

In one embodiment, proximal portion 110 has a length between about 12.7 mm and about 127.0 mm. In another embodiment, proximal portion 110 has a length between about 25.4 mm and about 88.9 mm. In another embodiment, proximal portion 110 has a length between about 38.1 mm and about 63.5 mm. In one embodiment, the tapered junction between proximal portion 110 and distal portion 112 has a length between about 5.1 mm and about 50.8 mm. In another embodiment, the tapered junction between proximal portion 110 and distal portion 112 has a length between about 10.2 mm and about 30.5 mm. In another embodiment, the tapered junction between proximal portion 110 and distal portion 112 has a length between about 12.7 mm and about 25.4 mm.

In one embodiment, proximal portion 110 comprises a diameter and wall thickness selected to obtain the necessary compressive, tensile, bending, or shear strength to compress and/or support any of various bone elements in a human or animal body. In another embodiment, proximal portion 110 comprises a diameter and wall thickness configured to receive larger transverse bolts through static fixation apertures 108 than may be used in distal portion 112.

In one embodiment, elongated shaft 102 comprises a proximal end 114 and a distal end 116. In one embodiment, proximal end 114 is open and is in communication with longitudinal inner bore 104. In another embodiment, distal end 116 is closed and is not in communication with longitudinal inner bore 104. In another embodiment, distal end 116 is at least partially tapered, which taper may assist in the insertion of apparatus 100 into a reamed bone element.

In one embodiment, elongated shaft 102 is substantially rigid. In another embodiment, elongated shaft 102 is at least partially rigid. Elongated shaft 102 may comprise any of a variety of materials, including one or more of a metal, an alloy, a composite, a polymer, or another organic material or biocompatible material. Elongated shaft 102 may comprise a compressive, tensile, bending, or shear strength as necessary to compress and/or support any of various bone elements in a human or animal body. Such compressive, tensile, bending, or shear strength may vary depending upon the application of apparatus 100, the forces to be supported, or the activity level of the patient.

FIG. 2 illustrates a longitudinal-sectional view of an example arrangement of an apparatus 200 for causing compression between bone elements. Apparatus 200 comprises an elongated shaft 202 having a longitudinal inner bore 204 extending longitudinally through at least a portion of elongated shaft 202.

Elongated shaft 202 comprises at least one compression slot 206 extending partially or completely across elongated shaft 202. In one embodiment, elongated shaft 202 comprises at least one static fixation aperture 208 extending partially or complete across elongated shaft 202.

In one embodiment, elongated shaft 202 comprises a proximal portion 210. In another embodiment, elongated shaft 202 comprises a proximal end 214.

Apparatus 200 may comprise at least one channel 218, 220 oriented longitudinally along at least a portion of longitudinal inner bore 204. In one embodiment, at least one channel 218, 220 is in communication with compression slot 206.

In one embodiment, apparatus 200 comprises two channels 218, 220. In another embodiment, two channels 218, 220 are substantially opposed to one another on either side of longitudinal inner bore 204. First channel 218 may extend along at least a portion of longitudinal inner bore 204 on a first side of longitudinal inner bore 204. Second channel 220 may extend along at least a portion of longitudinal inner bore 204 on a second side of longitudinal inner bore 204. The first and second sides of longitudinal inner bore 204 may be substantially opposed. First channel 218 and second channel 220 may be about 180 degrees from one another within longitudinal inner bore 204. In one embodiment, first channel 218 or second channel 220 are recessed into the wall of elongated shaft 202 along longitudinal inner bore 204 as grooves. In another embodiment, first channel 218 or second channel 220 are defined by pairs of lands extending from the wall of elongated shaft 202 along longitudinal inner bore 204.

In one embodiment, first channel 218 and second channel 220 are substantially parallel and extend along at least a portion of longitudinal inner bore 204 in two substantially straight lines. In one embodiment, first channel 218 and second channel 220 define a first plane, and compression slot 206 and static fixation aperture 208 extend about axes that are substantially perpendicular to the first plane.

In another embodiment, first channel 218 and second channel 220 are substantially helical and extend along at least a portion of longitudinal inner bore 204 in two substantially spiraled lines. First channel 218 and second channel 220 may extend about at least a portion of longitudinal inner bore 204 similar to rifling in a firearm barrel. In one embodiment, a first circular aperture 208 extends along a first axis at a first point along longitudinal inner bore 204, a second circular aperture 208 extends along a second axis at a second point along longitudinal inner bore 204, and compression slot 206 extends along a third axis at a third point along longitudinal inner bore 204 (wherein any of first, second, and third axes may be substantially parallel or perpendicular in relation to one another). In this embodiment, first channel 218 and second channel 220 may have a helical relationship and may be configured such that first channel 218 and second channel 220 straddle the first axis at a first point along longitudinal inner bore 204, straddle the second axis at a second point along longitudinal inner bore 204, and straddle the third axis at a third point along longitudinal inner bore 204, such that first channel 218 and second channel 220 extend uninterrupted along longitudinal inner bore and communicate with compression slot 206.

In one embodiment, apparatus 200 comprises a fastening member 222 configured to at least temporarily attach at least one of a guide and a tensioning device to apparatus 200. Fastening member 222 may include threads configured to mate with threads on at least one of a guide and a tensioning device.

FIG. 3 illustrates a cross-sectional view of an example arrangement of an apparatus 200 for causing compression between bone elements. Apparatus 200 comprises an elongated shaft 202 having a longitudinal inner bore 204 extending longitudinally through at least a portion of elongated shaft 202. First channel 218 and second channel 220 are substantially opposed on either side of longitudinal inner bore 204.

Figure 4:
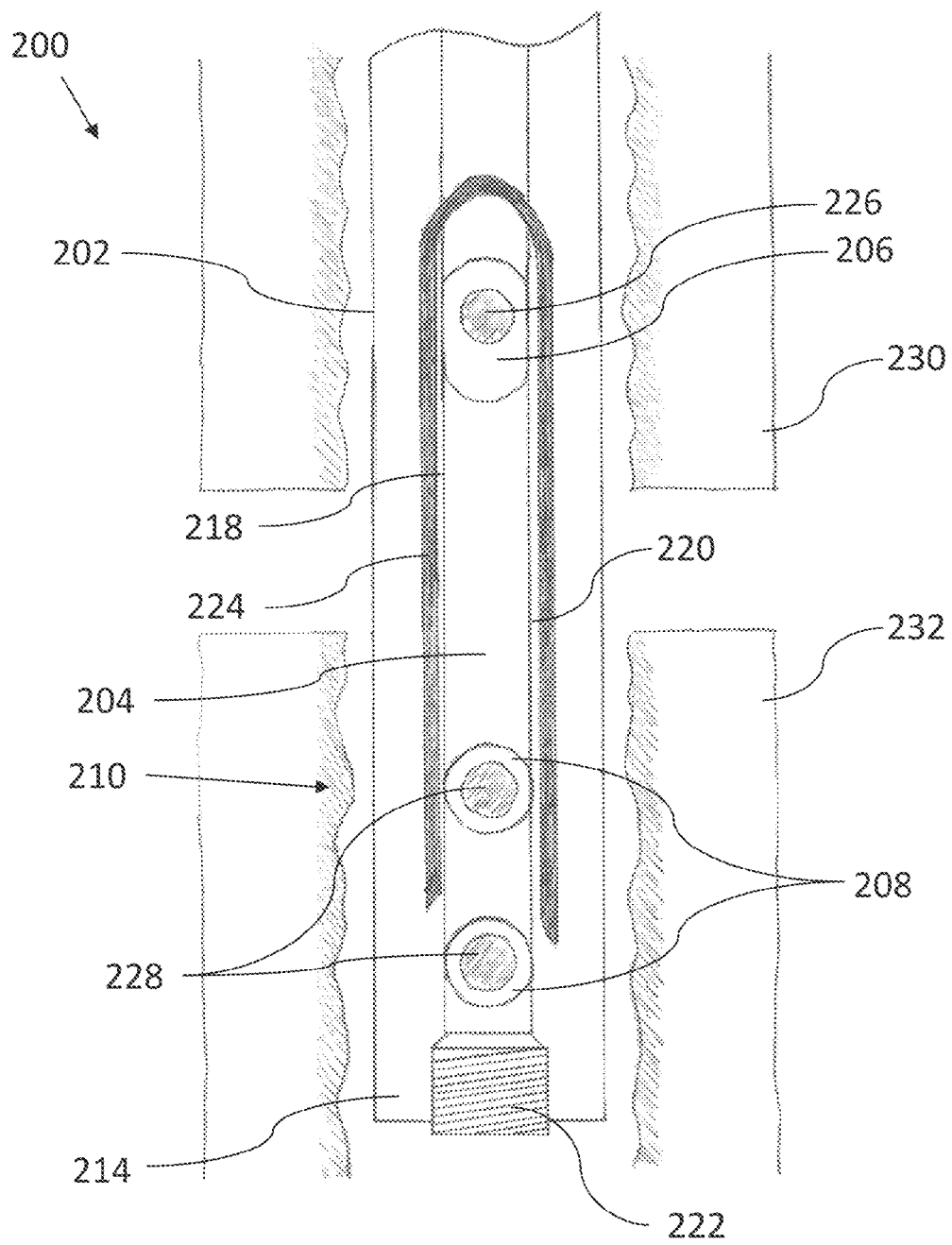
FIG. 4 is a longitudinal-sectional view of an example arrangement of an apparatus for causing compression between bone elements.

FIG. 4 illustrates a longitudinal-sectional view of an example arrangement of an apparatus 200 for causing compression between bone elements. Apparatus 200 comprises an elongated shaft 202 having a longitudinal inner bore 204 extending longitudinally through at least a portion of elongated shaft 202. First channel 218 and second channel 220 are substantially opposed on either side of longitudinal inner bore 204.

Elongated shaft 202 comprises at least one compression slot 206 extending partially or completely across elongated shaft 202. In one embodiment, elongated shaft 202 comprises at least one static fixation aperture 208 extending partially or complete across elongated shaft 202.

In one embodiment, elongated shaft 202 comprises a proximal portion 210. In another embodiment, elongated shaft 202 comprises a proximal end 214.

Apparatus 200 may comprise at least one channel 218, 220 oriented longitudinally along at least a portion of longitudinal inner bore 204. In one embodiment, at least one channel 218, 220 is in communication with compression slot 206. In one embodiment, at least one channel 218, 220 comprises a first channel 218 and a second channel 220.

In one embodiment, apparatus 200 comprises at least one tensioning cable 224. In one embodiment, at least one channel 218, 220 is configured to accept tensioning cable 224. The term cable may be used interchangeably with tensioning cable herein.

In one embodiment, tensioning cable 224 extends from proximal end 214 of elongated shaft 202, through first channel 218, about a portion of compression slot 206, and through second channel 220 back to proximal end 214. In one embodiment, compression slot 206 is configured to accept a first transverse bolt 226, and tensioning cable 224 extends about a portion of first transverse bolt 226. In one embodiment, tensioning cable 224 extends about and contacts at least the distal portion of first transverse bolt 226.

Tensioning cable 224 may be any flexible elongated cable, wire, string, chain, rope, cord, or fiber. In one embodiment, tensioning cable 224 is a substantially solid single strand of material. In another embodiment, tensioning cable 224 comprises braided or otherwise linked multiple strands of material. In one embodiment, tensioning cable 224 is comprised of any of a variety of materials, including one or more of a metal, an alloy, a composite, a polymer, or another organic material or biocompatible material.

In one embodiment, tensioning cable 224 is substantially resilient, and exerts force to resist bending. In another embodiment, tensioning cable 224 may comprise a spring element to achieve adequate resiliency. In one embodiment, tensioning cable 224 may comprise a resiliency adequate to cause tensioning cable 224 to exert forces radially outwardly upon longitudinal inner bore 204, first channel 218, and second channel 220. That is, tensioning cable 224 may be bent and inserted first channel 218 and second channel 220, wherein the resiliency of tensioning cable 224 will cause it to exert radially outward forces that cause tensioning cable 224 to maintain its position within first channel 218 and second channel 220.

In one embodiment, tensioning cable 224 comprises adequate tensile strength to compress and/or support any of various bone elements in a human or animal body. In one embodiment, tensioning cable 224 is configured to compress any of a joint, fracture, or otherwise adjacently-oriented bone elements.

In one embodiment, tensioning cable 224 is used temporarily to compress and/or support any of various bone elements in a human or animal body. In one embodiment, tensioning cable 224 is removably attached to elongated shaft 202. In another embodiment, tensioning cable 224 is removed following temporary compression and/or support of any of various bone elements in a human or animal body.

In one embodiment, at least one static fixation aperture 208 is configured to accept a second transverse bolt 228.

Apparatus 200 may be configured to cause compression between a plurality of bone elements, including a first bone element 230 and a second bone element 232. In one embodiment, elongated shaft 202 of apparatus 200 is configured to span a junction between at least two bone elements, such as first bone element 230 and second bone element 232. In another embodiment, apparatus 200 is configured to span three or more bone elements, and may impart compressive force directly upon the most distally and proximally oriented elements, and indirect force on intermediate elements. Such indirect force may be similar to a clamping force, wherein one or more intermediate elements are sandwiched between two or more clamping elements.

In practice, a hole may be reamed through one or more bone elements, such as first bone element 230 and second bone element 232. Apparatus 200 may be inserted into the reamed hole, distal end first. Tensioning cable 224 may be extended through first channel 218 and second channel 220 to a point distal of compression slot 206. First transverse bolt 226 may be extended at least partially through first bone element 230 and the distal portion of compression slot 206 so as to substantially fix first transverse bolt 226 to first bone element 230 while allowing longitudinal movement between elongated shaft 202 and first bone element 230. Second transverse bolt 228 may be extended at least partially through second bone element 232 and static fixation aperture 208 so as to substantially fix second transverse bolt 228 and elongated shaft 202 to second bone element 232.

A tensioning device (not shown) may be at least temporarily attached to apparatus 200, for example via fastening member 222. The tensioning device may be configured to impart tension upon tensioning cable 224. When the tensioning device imparts tension upon tensioning cable 224, tensioning cable 224 contacts at least the distal portion of first transverse bolt 226, and draws first transverse bolt 226, and thus first bone element 230, proximally toward second bone element 232. The tensioning device may continue to impart increased tension upon tensioning cable 224 until at least one of: (a) first bone element 230 and second bone element 232 are at a desired distance from one another; (b) first bone element 230 and second bone element 232 are contacting one another; (c) first bone element 230 and second bone element 232 are compressed against one another; and (d) first bone element 230 and second bone element 232 are compressed against one another with a desired amount of compression.

Upon achieving desired positioning of first bone element 230 and second bone element 232, a third transverse bolt (not shown) may be inserted through a static fixation aperture in the distal portion of elongated shaft 202 as illustrated in FIG. 2. The insertion of the third transverse bolt through a static fixation aperture in the distal portion of elongated shaft 202 may substantially fix elongated shaft 202 to first bone element 230. At this point, first bone element 230 and second bone element 232 are maintained in position by two or more transverse bolts in static fixation apertures 208, such that elongated shaft 202 is maintaining the desired position and/or compression of first bone element 230 and second bone element 232. Tensioning cable 224 is no longer required to maintain the desired position and/or compression of first bone element 230 and second bone element 232.

The tensioning device (not shown) may be removed from apparatus 200. Tensioning cable 224 may be pulled about a first end extending from first channel 218 and drawn up second channel 220, over first transverse bolt 226, and down first channel 218 and out of elongated shaft 202. Alternatively, tensioning cable 224 may be pulled about a second end extending from second channel 220. Tensioning cable 224 may be discarded at this point, or processed for use in later operations.

Apparatus 200 may be used to draw any two bone elements together. In one embodiment, apparatus 200 may be used in the fusion of any joint in a human or animal body.

Figure 5A:
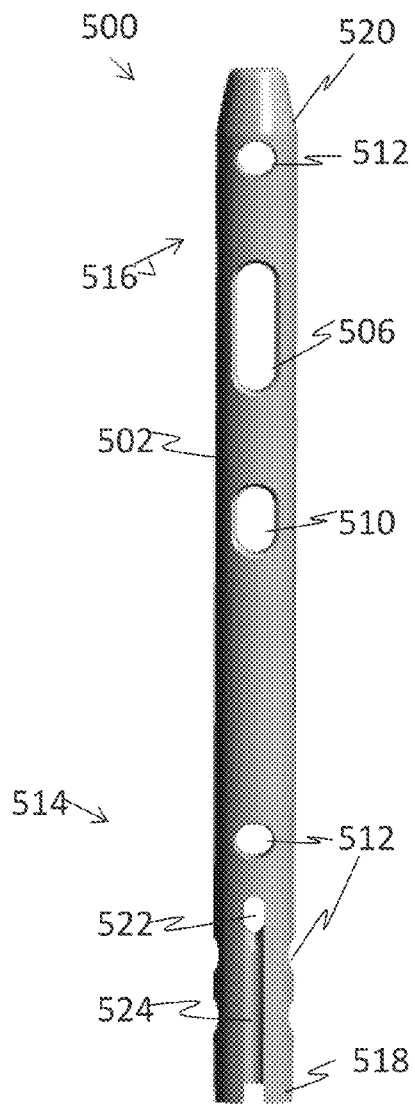
FIG. 5A is a top elevational view of an example arrangement of an apparatus for causing compression between bone elements.
Figure 5B:
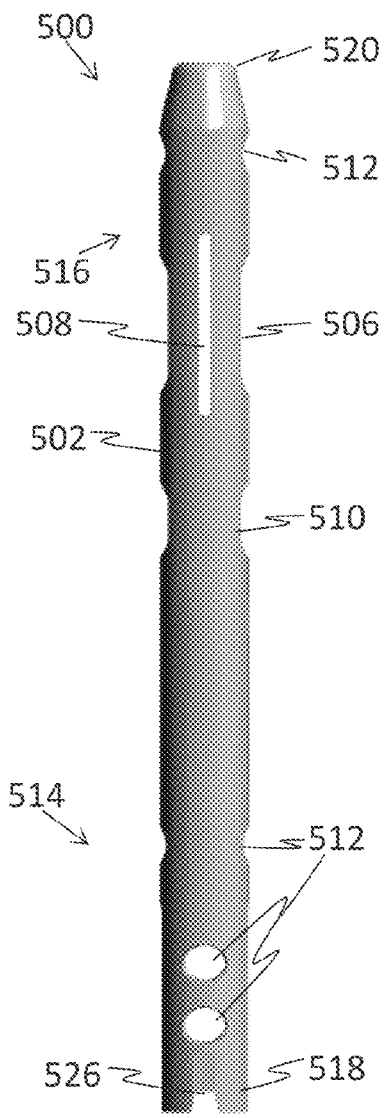
FIG. 5B is a side elevational view of the example arrangement of an apparatus for causing compression between bone elements of FIG. 5A rotated 90 degrees about the longitudinal axis.

FIGS. 5A and 5B are top and side elevational views, respectively, of an example arrangement of an apparatus 500 for causing compression between bone elements. Apparatus 500 may include an elongated shaft 502 having a longitudinal inner bore (not shown in FIGS. 5A and 5B, but shown as longitudinal inner bore 704 in FIG. 7) extending longitudinally through at least a portion of elongated shaft 502.

Elongated shaft 502 may include at least one compression slot 506 extending partially or completely across elongated shaft 502. Compression slot 506 may be configured to accept a transverse bolt (not shown), which may extend across at least a portion of elongated shaft 502. The transverse bolt may be configured to connect to a bone element. In another embodiment, the transverse bolt may be used to interface with a tensioning cable to cause compression between bone elements.

In one embodiment, elongated shaft 502 may include at least one static fixation aperture 512 extending partially or complete across elongated shaft 502. In another embodiment, elongated shaft 502 may include a plurality of static fixation apertures 512. Static fixation aperture 512 may be configured to accept a transverse bolt (not shown). The transverse bolt may extend across at least a portion of elongated shaft 502. The transverse bolt may be configured to connect to a bone element. In one embodiment, static fixation aperture 512 may be connected to and in communication with the longitudinal inner bore. In another embodiment, static fixation aperture 512 may not be connected to or in communication with the longitudinal inner bore such that a transverse bolt securing elongated shaft 502 to a bone element via static fixation aperture 512 may not interfere with compression devices within the longitudinal inner bore.

In one embodiment, the transverse bolt may include any of a temporary or permanent bolt, screw, or pin. In another embodiment, the transverse bolt may include a locking screw. In another embodiment, the transverse bolt may include any fastening device capable of joining elongated shaft 502 to a bone element.

Referring now to FIG. 5A, elongated shaft 502 may include one or more dynamization slots 510. Dynamization slot 510 may be used in addition to static fixation aperture 512 to secure apparatus 500 to a bone segment using a transverse bolt (not shown). Compared to static fixation aperture 512, dynamization 510 slot may be oblong and vary in shape to allow for some dynamic movement of apparatus 500 relative to a bone segment, when apparatus 500 may be secured to a bone segment with a transverse bolt through dynamization slot 510. In one embodiment, securing apparatus 500 to a fixed to a bone segment with a transverse bolt through dynamization slot 510 aids in joint fusion and promotes growth between joints compared to a static fixation using static fixation aperture 512.

In one embodiment, elongated shaft 502 may include a proximal portion 514 and a distal portion 516. In one embodiment, proximal portion 514 may include a greater diameter than distal portion 516. In another embodiment, proximal portion 514 may include a diameter substantially the same as distal portion 516. In another embodiment, proximal portion 514 may include a lesser diameter than distal portion 516. In one embodiment, the junction between proximal portion 514 and distal portion 516 may be tapered.

In one embodiment, proximal portion 514 has a length between about 10.0 mm and about 130.0 mm. In another embodiment, proximal portion 514 has a length between about 25.0 mm and about 90.0 mm. In another embodiment, proximal portion 514 has a length between about 35.0 mm and about 65.0 mm.

In one embodiment, proximal portion 514 may include a diameter and wall thickness selected to obtain the necessary compressive, tensile, bending, or shear strength to compress and/or support any of various bone elements in a human or animal body. In another embodiment, proximal portion 514 may include a diameter and wall thickness configured to receive larger transverse bolts through static fixation apertures 512 than may be used in distal portion 516.

In one embodiment, elongated shaft 502 may include a diameter in a range of about 5.0 mm to about 15.0 mm. In another embodiment, elongated shaft 502 may include a diameter in a range of about 10.0 mm to about 20.0 mm.

In one embodiment, elongated shaft 502 may include a proximal end 518 (inferior) and a distal end 520 (superior). In one embodiment, proximal end 518 may be closed and may not be in communication with the longitudinal inner bore. In another embodiment, distal end 520 may be open and may be in communication with the longitudinal inner bore. In another embodiment, distal end 520 may be at least partially tapered. The partial taper may assist in the insertion of apparatus 500 into a reamed bone element.

With continued reference to FIG. 5A, proximal portion 514 of elongated shaft 502 may include one or more tensioning cable apertures 522. Tensioning cable aperture 522 may be in communication with the longitudinal inner bore such that a tensioning cable may enter and exit the longitudinal inner bore or elongated shaft 502 through tensioning cable aperture 522. In one embodiment, apparatus 500 may have two tensioning cable apertures 522 diametrically opposed on external surface of elongated shaft 502. Both tensioning cable apertures 522 may be in communication with the longitudinal inner bore such that a loop of tensioning cable may be inserted within the longitudinal inner bore. One end of tensioning cable may exit one tensioning cable aperture 522 and another end of tensioning cable may exit a diametrically opposed tensioning cable aperture 522, leaving a loop of tensioning cable remaining within the longitudinal inner bore. In one embodiment, tensioning cable aperture 522 may also be in communication with tensioning cable routing channel 524. Tensioning cable routing channel 524 may be machined into an external surface of elongated shaft 502 to secure and route a tensioning cable going into and coming out of the longitudinal inner bore through tensioning cable aperture 522. In one embodiment, tensioning cable routing channel 524 may be used to secure a tensioning cable to avoid unwanted contamination during a medical procedure.

Referring now to FIG. 5B, elongated shaft may include at least one tensioning cable clearance slot 508. In one embodiment, tensioning cable clearance slot 508 may be in communication with the longitudinal inner bore and may extend radially from the longitudinal inner bore to the external surface of elongated shaft 502. Tensioning cable clearance slot 508 may be offset about 90 degrees from compression slot 506. In one embodiment, tensioning cable clearance slot 508 may traverse elongated shaft 502 such that apparatus 500 may have two tensioning cable clearance slots 508 diametrically opposed from each other. Compression slot 506 may traverse elongated shaft 502 such that apparatus 500 may have two compression slots 506 diametrically opposed from each other and offset about 90 degrees from clearance slots 508. Tensioning cable clearance slot 508 may be used to allow a loop formed from a length of tensioning cable within the longitudinal inner bore to bow outwardly from the longitudinal inner bore through tensioning cable clearance slot 508. In one embodiment, a loop of tensioning cable within the longitudinal inner bore extending through tensioning cable clearance slot 508 may not interfere with insertion of transverse bolts or other securing member through compression slot 506 during a medical procedure. In another embodiment, a loop of tensioning cable extending from tensioning cable clearance slot 508 may direct tensioning cable within the longitudinal inner bore to an outer region of the longitudinal inner bore such that tensioning cable within the longitudinal inner bore may not interfere with the transverse bolts. Also, tensioning cable within the longitudinal inner bore may not interfere with the insertion and removal of the transverse bolts or other securing members in static fixation aperture 512 and dynamization slot 510.

With continued reference to FIG. 5B, elongated shaft 502 may have one or more support device engagement notches 526 machined on proximal end 518. One or more support device engagement notches 526 may interface apparatus 500 with a support device to be used in a system for causing compression of bone elements.

In one embodiment, elongated shaft 502 may be substantially rigid. In another embodiment, elongated shaft 502 may be at least partially rigid. Elongated shaft 502 may include any of a variety of materials, including one or more of a metal, an alloy, a composite, a polymer, or another organic material or biocompatible material. Elongated shaft 502 may include a compressive, tensile, bending, or shear strength effective to compress and/or support bone elements in a human or animal body. Such compressive, tensile, bending, or shear strength may vary depending upon the application of apparatus 500, the forces to be supported, or the activity level of the patient. In one embodiment, elongated shaft 502 may be of a material that may be radio translucent (radiolucent) to assist in imaging techniques such as Mill and X-ray. In another embodiment, elongated shaft 502 may be of a material that may be non-radiolucent.

FIG. 6 is a perspective view of a proximal end of an example arrangement of an apparatus 600 for causing compression between bone elements. Apparatus 600 may include an elongated shaft 602, one or more compression slots 606, one or more tensioning cable clearance slots 608 offset about 90 degrees from compression slot 606, one or more dynamization slots 610, and one or more static fixation apertures 612. In addition, an external surface of elongated shaft may include a machined portion used as a tensioning cable routing channel 624 and one or more support device engagement notches 626. In one embodiment, apparatus 600 may include nail fastener engagement 628 on the longitudinal axis of elongated shaft 602 and located on an inferior face of elongated shaft 602. Nail fastener engagement 628 may include common mechanical connection such that a nail fastener (not shown) may engage apparatus 600. Such common mechanical connections may include threads, press fittings, bayonet fittings and the like. Nail fastener engagement 628 may be threaded to interface with threads of a nail fastener (not shown).

FIG. 7 is a perspective view of a distal end of an example arrangement of an apparatus 700 for causing compression between bone elements. Apparatus 700 may include distal end 720 with distal aperture 730 in communication with longitudinal inner bore 704. Distal aperture 730 may be used to assist in forming a loop of tensioning cable within longitudinal inner bore 704.

Figure 8:
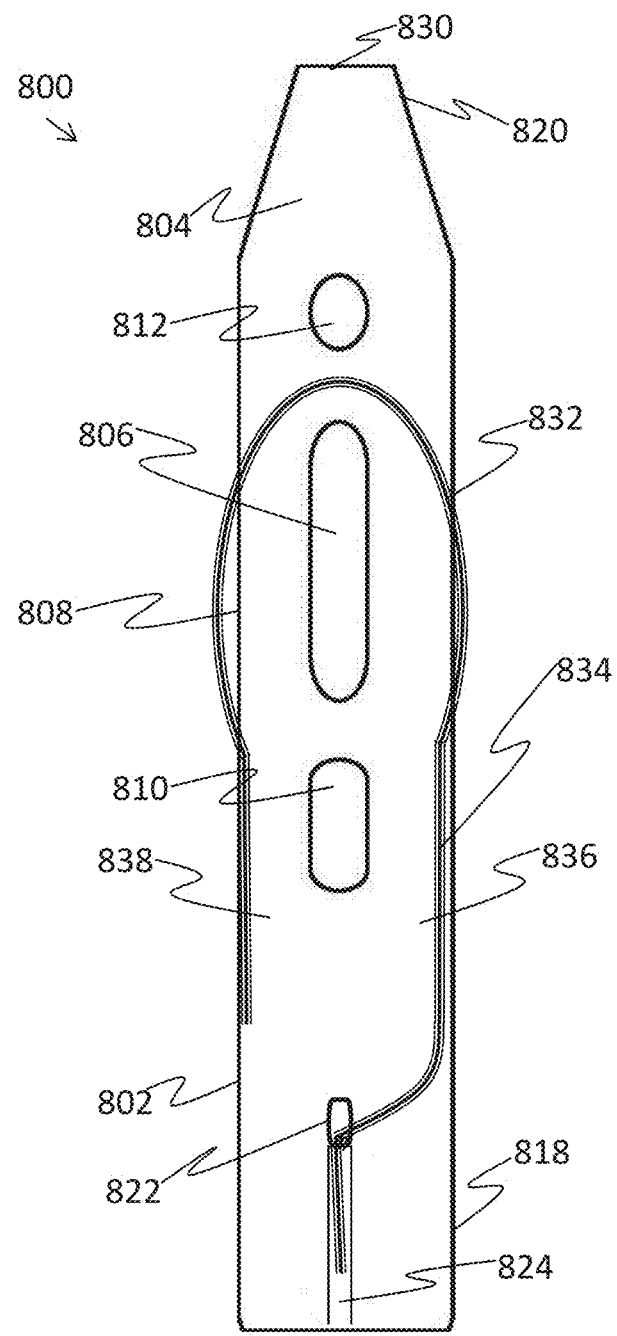
FIG. 8 is a longitudinal cross-sectional view of an example arrangement of an apparatus for causing compression between bone elements.

FIG. 8 is a longitudinal cross-sectional view of an example arrangement of an apparatus 800 for causing compression between bone elements. Longitudinal inner bore 804 may allow for a length of tensioning cable 834 to form a loop 832 within longitudinal inner bore 804. Loop 832 may bow outwardly through tensioning cable clearance slots 808. In one embodiment, loop 832 may direct tensioning cable 834 to sides 836 and 838 of longitudinal inner bore 804 such that tensioning cable 834 may not interfere with the insertion of transverse bolts (not shown) passing through compression slot 806, dynamization slot 810 and static fixation aperture 812. In one embodiment, tensioning cable 834 may make an about 90 degree helical twist before passing from longitudinal inner bore 804 through tensioning cable aperture 822. In one embodiment, tensioning cable 834 passing into and from tensioning cable aperture 822 may be contained and secured within tensioning cable routing channel 824.

Tensioning cable 834 may be preloaded such that tensioning cable loop 832 runs through tensioning cable clearance slots 808 with tensioning cable 834 inside longitudinal inner bore 804, such that the ends of tensioning cable 834 exiting tensioning cable apertures 822 may be positioned prior to apparatus 800 being used in a medical procedure. In one embodiment, apparatus 800 with preloaded tensioning cable 834 may be pre-packaged in a sterilized packaging for use during a medical procedure. Tensioning cable 834 may be preloaded into apparatus 800 in a manufacturing facility using a manufacturing process. In another embodiment, tensioning cable 834 may be loaded by hand such that tensioning cable loop 832 may extend outwardly through tensioning cable clearance slots 808 such that tensioning cable 834 may not interfere with an insertion of transverse bolts into compression slot 806, dynamization slot 810, and static fixation aperture 812, with tensioning cable 834 making an about 90 degree helical twist within longitudinal inner bore 804 before the end of tensioning cable 834 exits through tensioning cable apertures 822. For example, a device such as a hooked tool may be used to manipulate the tensioning cable within longitudinal inner bore 804 through distal aperture 830.

Tensioning cable 834 may be any flexible elongated tensioning cable, wire, string, chain, rope, cord, or fiber. In one embodiment, tensioning cable 834 may be a substantially solid single strand of material. In another embodiment, tensioning cable 834 may include braided or otherwise linked multiple strands of material. In one embodiment, tensioning cable 834 may include any of a variety of materials, including one or more of a metal, an alloy, a composite, a polymer, or another organic material or biocompatible material.

In one embodiment, tensioning cable 834 may be substantially resilient, and may exert force to resist bending. In another embodiment, tensioning cable 834 may include a spring element to achieve adequate resiliency. In one embodiment, tensioning cable 434 may include a resiliency effective to cause tensioning cable 834 to exert forces radially outwardly upon longitudinal inner bore 804. Tensioning cable 834 may be bent and inserted into longitudinal inner bore 804. The resiliency of tensioning cable 834 may exert radially outward forces that cause tensioning cable 834 to maintain its position proximate to sides 836 and 838 of longitudinal inner bore 804.

In one embodiment, tensioning cable 834 may include adequate tensile strength to compress and/or support bone elements in a human or animal body. In one embodiment, tensioning cable 834 may be configured to compress any of a joint, fracture, or otherwise adjacently-oriented bone elements.

In one embodiment, tensioning cable 834 may have a diameter in a range from about 0.1 mm to about 2.0 mm. In another embodiment, tensioning cable 834 may have a diameter in a range from about 1.0 mm to about 5.0 mm.

In one embodiment, a transverse bolt may be passed through compression slot 806 and tensioning cable 834 may be tensioned such that tensioning cable loop 832 may be drawn through tensioning cable clearance slots 808 into longitudinal inner bore 804. Tensioning cable loop 832 may interface with the transverse bolt passed through compression slot 806. In several embodiments, apparatus 800 may be partially fixed to two or more bone elements with, e.g., transverse bolts through at least one of compression slot 806, dynamization slot 810, and static fixation aperture 812. Tensioned cabled 834 may act on transverse bolt through compression slot 806 and may cause further compression between bone elements. A final fixation of apparatus 800 to bone elements with transverse bolts through, for example, dynamization slot 810 and static fixation aperture 812 may be possible when such compression has been achieved. In one embodiment, tensioning cable 834 may be removed from longitudinal inner bore 804 of apparatus 800 after final fixation of apparatus 800 to bone elements.

Figure 9:
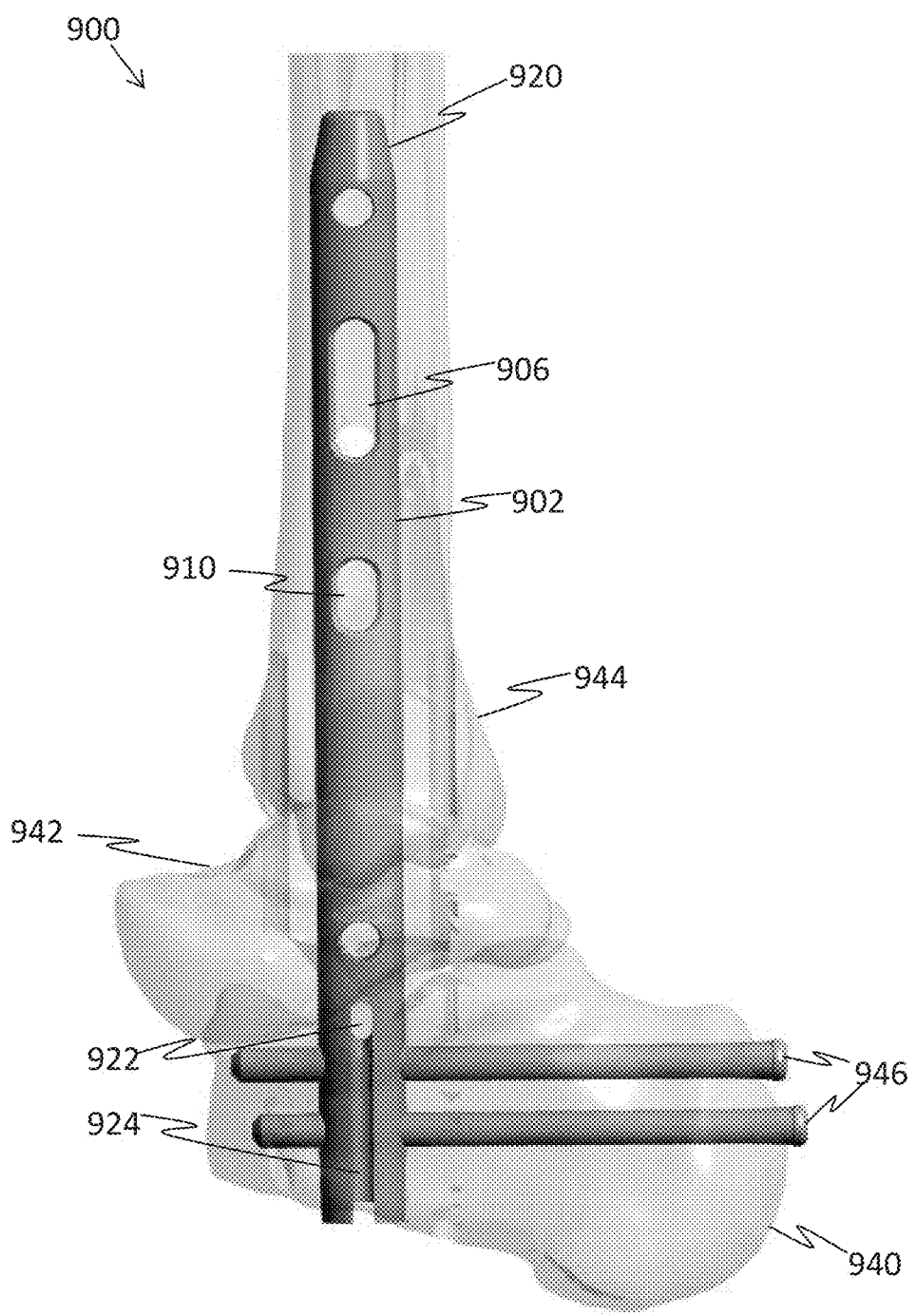
FIG. 9 is a top elevational view of an example arrangement of an apparatus for causing compression between bone elements within an example ankle joint.

FIG. 9 is a top elevational view of an example embodiment of apparatus 900 for causing compression between bone elements used in an example medical procedure. A lateral view of ankle bones within a human left foot is depicted. The example procedure may include a fusion procedure between bones and joints of calcaneus bone 940, talus bone 942, and tibia bone 944. For example, bones 940, 942, and 944 may be prepared to receive apparatus 900. Portions of bones 940, 942, and 944 may be reamed to a diameter of apparatus 900 to provide a proper fit of apparatus 900 within bones 940, 942, and 944. In this example embodiment, distal end 920 of apparatus 900 may be first inserted into an inferior side of calcaneus bone 940 and pushed through calcaneus bone 940, talus bone 942 and tibia bone 944 until apparatus 900 may be positioned as shown in FIG. 9. Calcaneal screws 946 passing through calcaneus 940 and static fixation apertures 912 may be used to statically fix apparatus 900 relative to calcaneus 940. A transverse bolt (not shown) may be passed through compression slot 906 and anchored to tibia bone 944. A tensioning cable (not shown) may be disposed within a longitudinal inner bore (not shown) of elongated shaft 902 and may exit apparatus 900 via tensioning cable apertures 922 and may be contained within the tensioning cable routing channel. The ends the tensioning cable may interface with a separate, external tensioning device, and may be used to interface with the transverse bolt passed through compression slot 906 such that a tensioning of the tensioning cable may cause the tensioning cable to interact with the transverse bolt passing through compression slot 906 and anchored to tibia bone 944. The tensioned tensioning cable may draw bones 940, 942, and 944 together and compress the joints thereof together. When such tension may be achieved, a final fixation of apparatus 900 may be performed, for example, by securing apparatus 900 to bones 940, 942, and 944 with transverse bolts through static fixation apertures 912 and dynamization slot 910. The tensioning cable may be removed from apparatus 900 by pulling one end of the tensioning cable such that tensioning cable may be pulled through the longitudinal inner bore of apparatus 900 and out of tensioning cable aperture 922, leaving apparatus 900 fixed to bones 940, 942, and 944. Bones located in other parts of the body may be used with apparatus 900 for bone compression.

Figure 10:
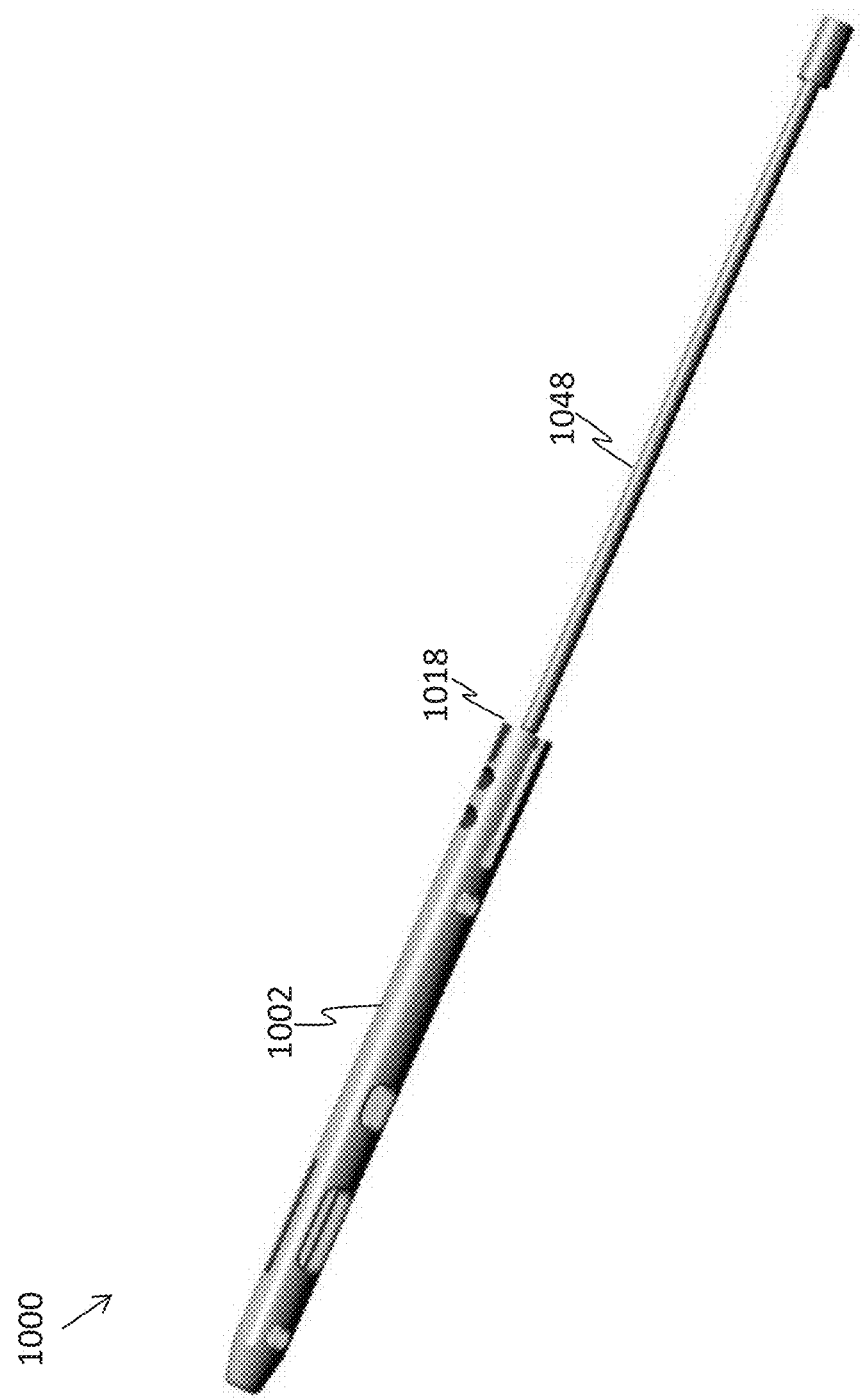
FIG. 10 is a perspective view of an example arrangement of an apparatus for causing compression between bone elements attached to a fastener.

FIG. 10 is a perspective view of an example arrangement of an apparatus 1000 for causing compression between bone elements as connected to a nail fastener 1048. Nail fastener 1048 may be used to interface apparatus 1000 to a system for causing compression between bone elements. In one embodiment, nail fastener 1048 may be used to manipulate apparatus 1000 within the body. Nail fastener 1048 may connect to 1000 via a nail fastener engagement (shown at 628 in FIG. 6, and described in previous paragraphs of this specification). Nail fastener 1048 may include a threaded end to interface with threads of nail fastener engagement 628. In another embodiment, nail fastener 1048 may use a different mechanical connection such as a press fitting, bayonet fitting, and the like, to connect with apparatus 1000.

Figure 11A:
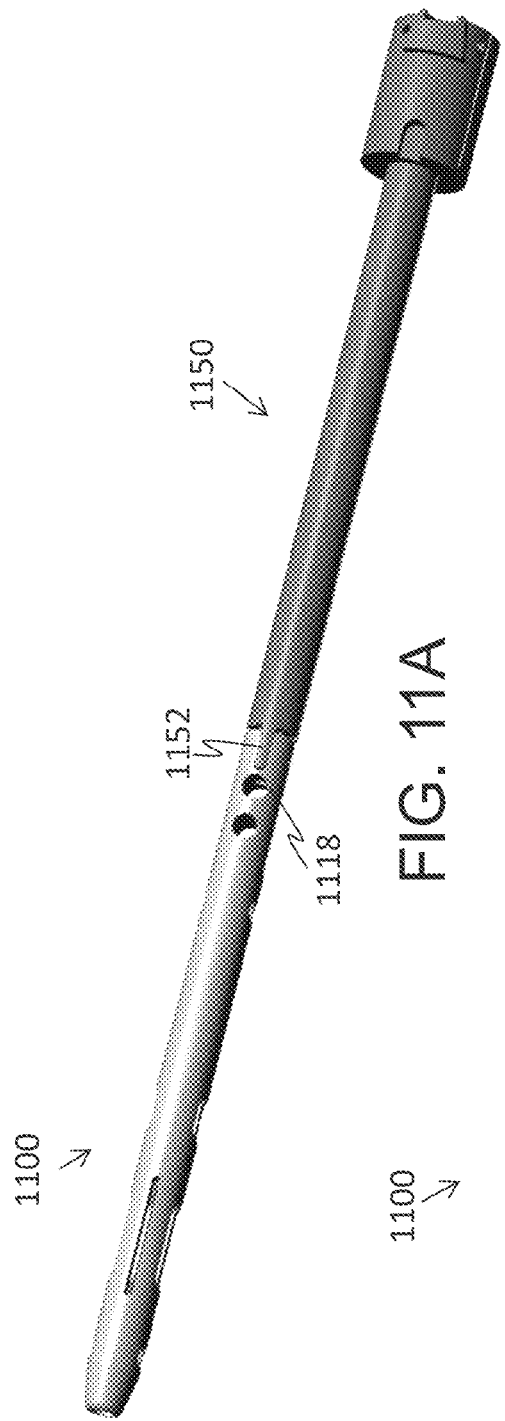
FIG. 11A is a perspective view of an example arrangement of an apparatus for causing compression between bone elements attached to a support device.
Figure 11B:
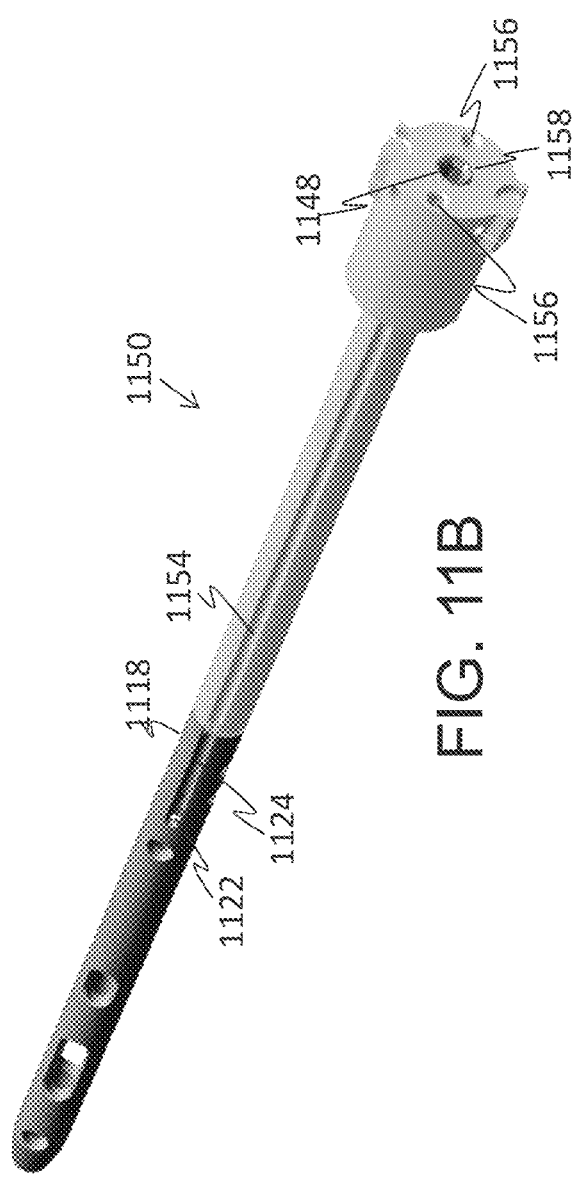
FIG. 11B is a perspective view of an example arrangement of an apparatus for causing compression between bone elements attached to a support device.

FIGS. 11A and 11B illustrate perspective views of an example arrangement of an apparatus 1100 for causing compression between bone elements as connected to support device 1150. Support device may be used to interface apparatus 1100 with a system for causing compression between bone elements. In one embodiment, support device 1150 may interface with apparatus 1100 at support device engagement notches 1126 disposed on distal end 1118 of elongated shaft 1102. Support device 1150 may include one or more engagement prongs 1152 which fit into and interface with engagement notches 1126. In one embodiment, support device 1150 may include one or more support device tensioning cable routing channels 1154 which may align with tensioning cable routing channel 1124 on apparatus 1100. Tensioning cables (not shown) exiting an inner bore of apparatus 1100 may be contained within tensioning cable routing channel 1124 and may be further contained in support device tensioning cable routing channel 1154, ultimately passing through support device tensioning cable apertures 1156 to further connect with a tensioning cable tensioning device (not shown). In one embodiment, tensioning cable routing channel 1124 and support device tensioning cable routing channel 1154 may secure a tensioning cable to prevent contamination of a tensioning cable during a medical procedure. In one embodiment, support device 1150 includes an inner bore 1158 extending the length of support device 1150 which allows support device to fit over nail fastener 1148.

Figure 12:
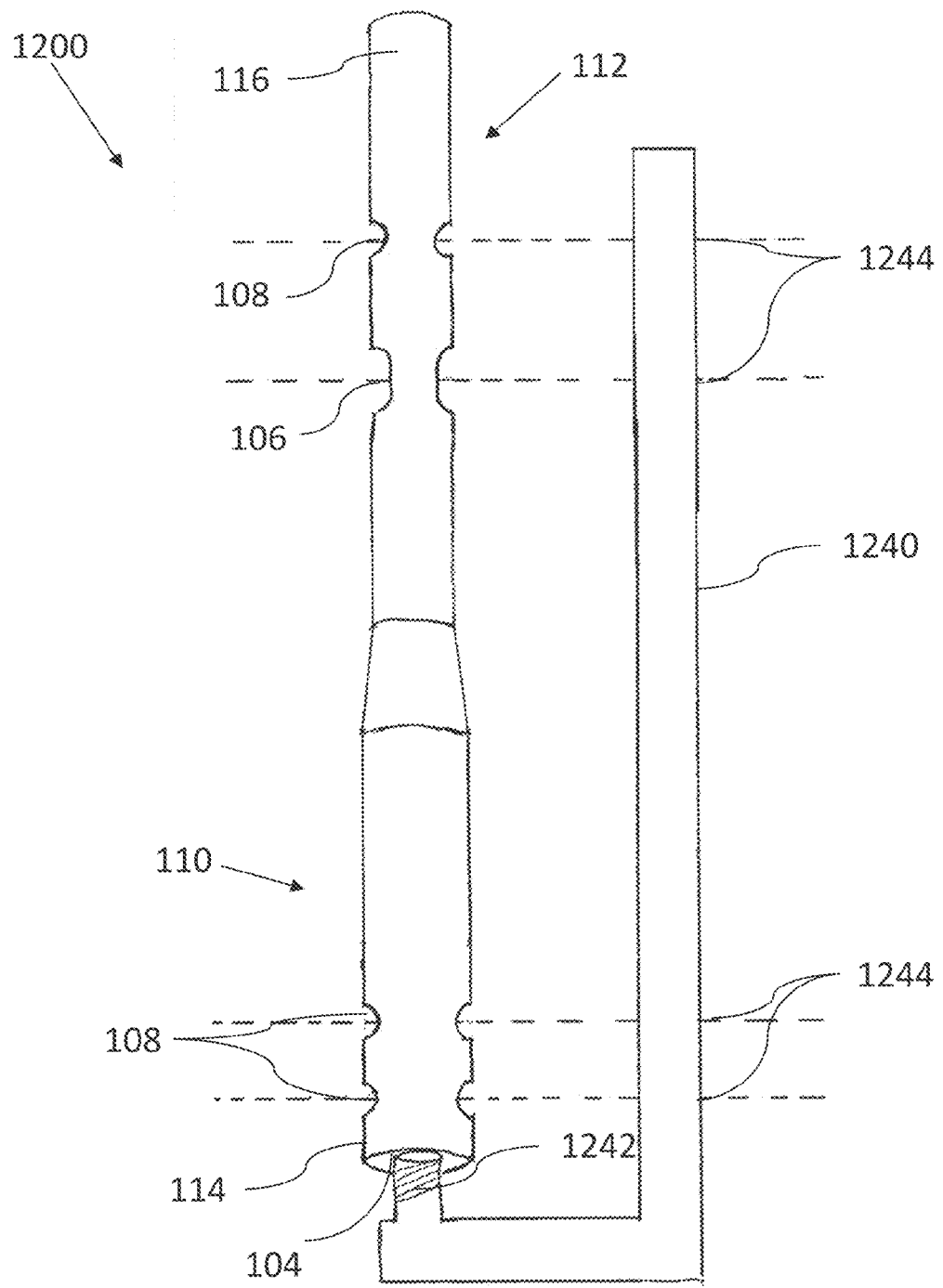
FIG. 12 is a perspective view of an example arrangement of a guide.

FIG. 12 illustrates a perspective view of an example arrangement of a guide 1240. Guide 1240 may be selectively attached to apparatus 100.

In one embodiment, guide 1240 comprises a connection member 1242 configured to selectively attach guide 1240 to apparatus 100. In one embodiment, connection member 1242 comprises a threaded shaft. In another embodiment, connection member 1242 comprises any fastening device capable of selectively attaching guide 1240 to apparatus 100. In another embodiment, connection member 1240 corresponds to fastening member (not shown) in distal end 114 of apparatus 100.

Guide 1240 may comprise a series of alignment holes 1244 about its length, which, when guide 1240 is coupled to apparatus 100, indicate the proper points at which to drill holes through tissue and/or bone elements to permit insertion of transverse bolts through at least one compression slot 106 and at least one static fixation aperture 108.

In one embodiment, apparatus 100 is inserted into the lower leg of a human to fuse the ankle joint and subtalar joint. Apparatus 100 may extend from the calcaneus bone, through the talus bone, and into the intramedullary canal of the tibia. In order to drill holes through the bone elements and into the at least one compression slot 106 and at least one static fixation aperture 108, a surgeon must advance a drill from outside the leg, ankle, and foot regions. Accordingly, the surgeon cannot see the at least one compression slot 106 and at least one static fixation aperture 108 to know where the holes must be drilled. Thus, guide 1240 provides alignment holes 1244, through which a drill is inserted to target the proper location and alignment of drilling from outside the leg to intersect the at least one compression slot 106 and at least one static fixation aperture 108.

Figure 13:
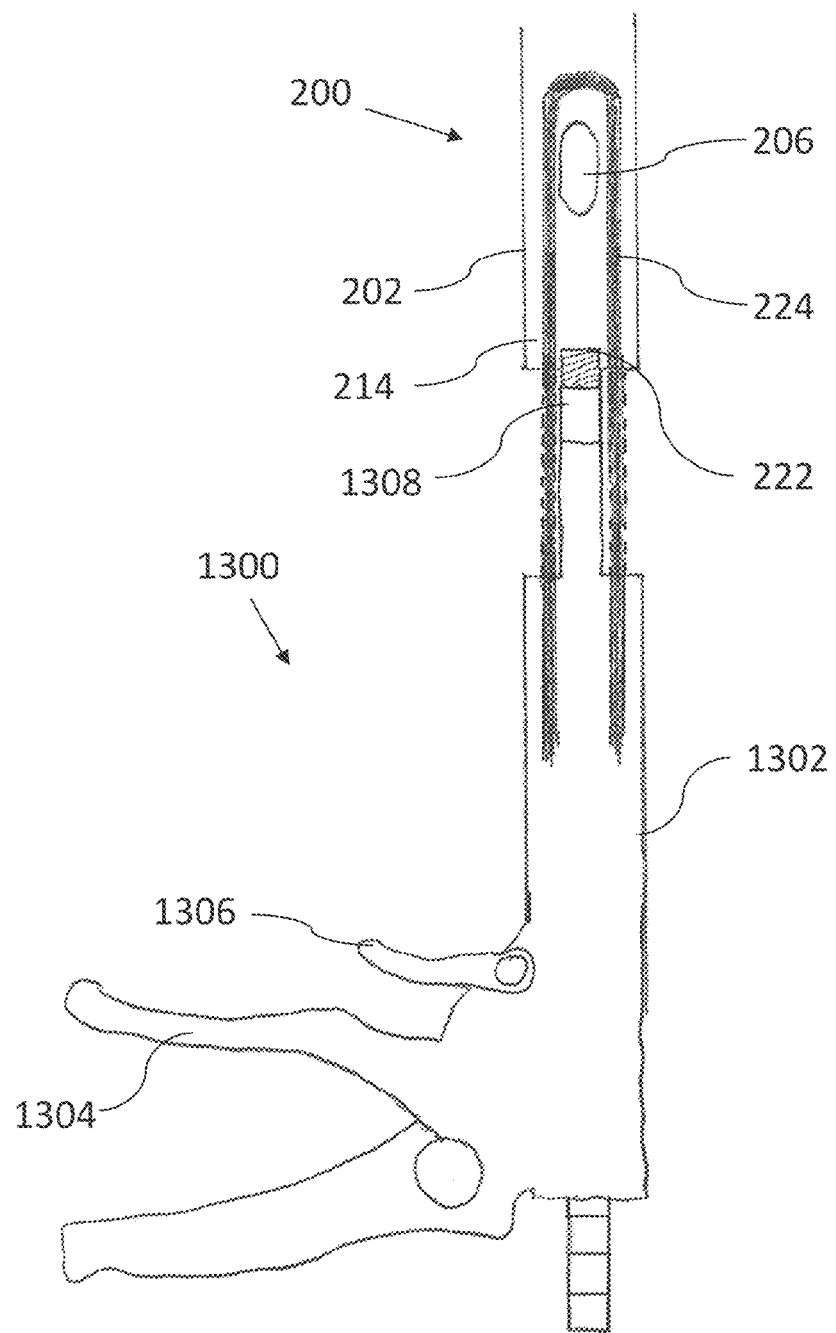
FIG. 13 is a top elevational view of an example arrangement of a tensioning device.

FIG. 13 illustrates a top elevational view of an example arrangement of a tensioning device 1300. Tensioning device 1300 may comprise a frame 1302, a lever 1304, a lock 1306, and an engagement mechanism 1308.

In one embodiment, tensioning device 1300 is removably connected to proximal end 214 of elongated shaft 202. In another embodiment, tensioning device 1300 is coupled to apparatus 200 via removable connection between fastening member 222 and engagement mechanism 1308. In another embodiment, engagement mechanism 1308 and fastening member 222 comprise male and female threads configured to engage one another.

In one embodiment, tensioning cable 224 is connected to tensioning device 1300. Lever 1304 may be actuated to draw at least one end of tensioning cable 224 into tensioning device 1300 to create and increase the tension in tensioning cable 224.

In one embodiment, tensioning device includes a lock 1306 configured to lock tensioning device 1300 so that it maintains a constant tension in tensioning cable 224. Lock 1306 may be selectively released to relieve tension in tensioning cable 224. Following tensioning and release of tension in tensioning cable 224, tensioning cable 224 may be disconnected from tensioning device 1300.

In one embodiment, tensioning device 1300 is configured to measure and indicate tension in tensioning cable 224. In another embodiment, tensioning device 1300 is configured to measure tension in tensioning cable 224 through any of various methods, including a force transducer, a strain gauge, and a spring tension gauge. In one embodiment, tensioning cable 224 includes an integrated force transducer, strain gauge, or spring tension gauge. In one embodiment, tensioning device 1300 is configured to indicate tension in tensioning cable 224 through any of various methods, including a digital display, an analog display, and a gauge.

Figure 14:
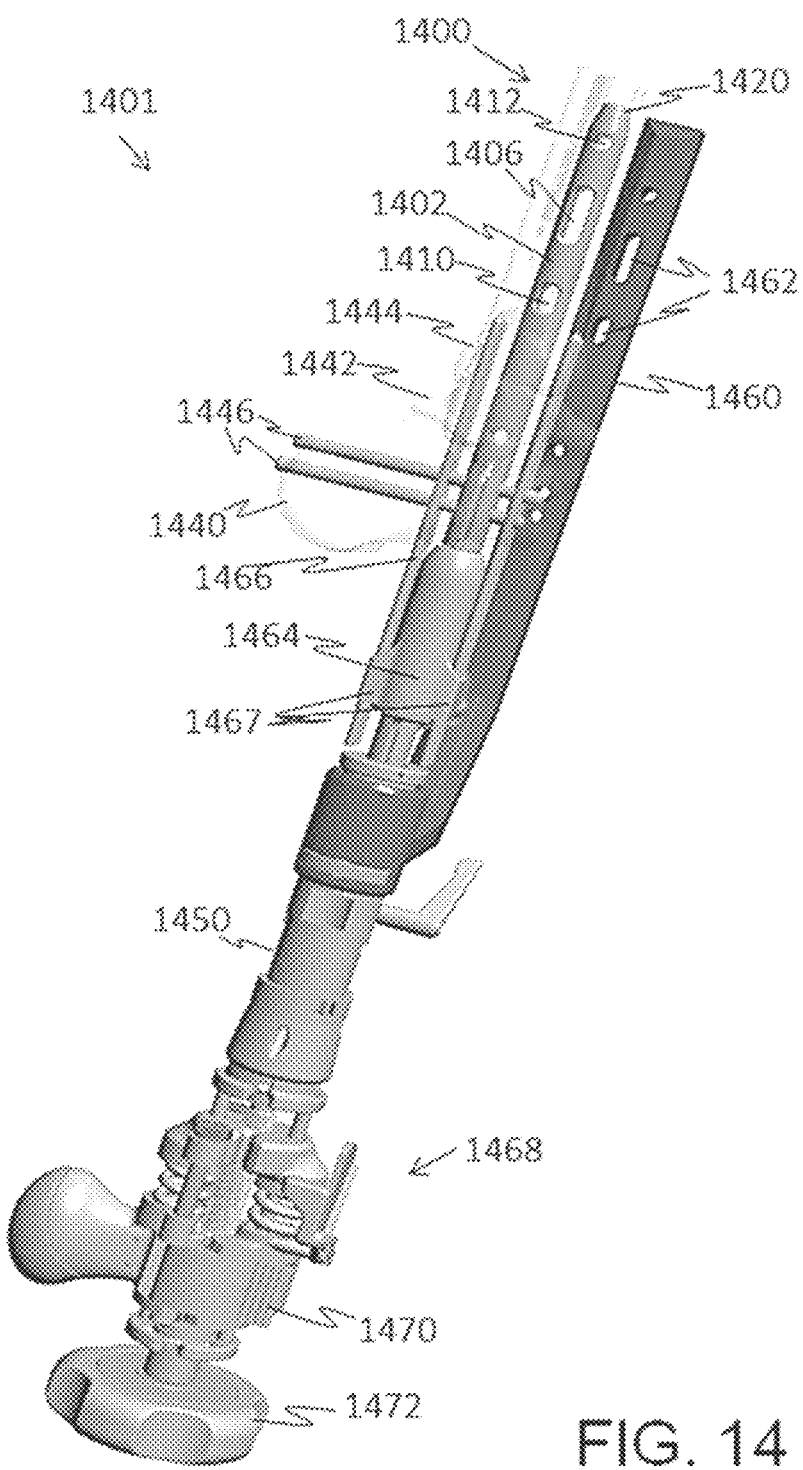
FIG. 14 is a perspective view of an example arrangement of an apparatus for causing compression between bone elements used in an example system for causing compression between bone elements.

FIG. 14 illustrates a perspective view of an example arrangement of a system 1401 for causing compression between bone elements as used in a medical procedure fusing ankle bones 1440, 1442, and 1444. FIG. 14 illustrates a medial view of bones 1440, 1442, and 1444 within a human left foot. System 1401 may include apparatus 1400 for causing compression between bone elements in addition to targeting arm 1460, protective sleeve 1464 and tensioning device 1468.

In an example embodiment, an apparatus 1400 for causing compression between bone elements may be inserted into bones 1440, 1442, and 1444. Before insertion of apparatus 1400, protective sleeve 1464 may be used to prepare bones 1440, 1442, and 1444 for insertion. Soft tissue on the bottom of the foot proximate to calcaneus 1440 may be excised to allow for at least partial insertion of protective sleeve 1464 into the soft tissue proximate to calcaneus 1440. Protective sleeve 1464 further may include an inner sleeve (not shown) which fits into and may be removable from protective sleeve 1464. After insertion of sleeve 1464 into the soft tissue at the bottom of the foot, one or more support rods 1466 may be inserted into support rod alignment apertures 1467 on protective sleeve 1464. Support rods 1466 may be drilled into bones 1440, 1442, and 1444 to hold protective sleeve 1464 in place within the soft tissue and relative to bones 1440, 1442, and 1444. An inner sleeve with a central guide for drilling a pilot hole may be inserted into protective sleeve 1464. A pilot hole may be drilled through bones 1440, 1442, and 1444 and inner sleeve may be removed from protective sleeve 1464. Inner-diameter of protective sleeve 1464 may be sized accordingly to match an outer diameter of apparatus 1400. Using the drilled pilot hole as a guide, protective sleeve 1464 may be used as a guide to ream the full outer diameter of apparatus 1400 from bones 1440, 1442, and 1444. Accordingly, inner diameter of protective sleeve 1464 may vary based on the outer diameter size of apparatus 1400 to be inserted, and inner sleeve diameter may vary accordingly to provide a desired fit between inner sleeve and protective sleeve 1464. Protective sleeve 1464 protects surrounding soft tissue during the drilling and reaming of bones 1440, 1442, and 1444. After bones are reamed to the appropriate diameter, targeting arm 1462 may be used to drill apertures through bones 1440, 1442, and 1444. Referring to system 1401 targeting arm 1460, targeting arm 1460 may have multiple apertures 1462 corresponding to apertures of compression slot 1406, dynamization slot 1410, and static fixation apertures 1412 on apparatus 1400. Targeting arm 1460 may be used as a guide to drill apertures corresponding to compression slot 1406, dynamization slot 1410, and static fixation apertures 1412 through bones 1440, 1442, and 1444. Target arm 1460 may rotate in intervals of about 90 degrees to match the about 90 degree offset of apertures corresponding to compression slot 1406, dynamization slot 1410, and static fixation apertures 1412 on apparatus 1400 such that apertures drilled through bones 1440, 1442, and 1444 may match apertures of compression slot 1406, dynamization slot 1410, and static fixation apertures 1412 on apparatus 1400 once apparatus 1400 may be inserted into bones 1440, 1442, and 1444. After apertures are drilled through bones 1440, 1442, and 1444, distal end 1420 of elongated shaft 1402 may be inserted through protective sleeve 1464 and through 1440, 1442, and 1444 until desired alignment of apparatus 1400 relative to the drilled bone apertures may be achieved. Nail fastener (not shown) may be used to manipulate apparatus 1400 to achieve proper alignment within the body. Once apparatus 1400 may be aligned, calcaneal screws 1446 may be inserted through calcaneus 1440 and through corresponding static fixation apertures on apparatus 1400 to partially, statically fix apparatus 1400 relative to bones 1440, 1442, and 1444. A transverse bolt may be inserted through the corresponding drilled aperture in tibia 1444 for compression slot 1406 and through compression slot 1406. A tensioning cable (not shown) within an inner longitudinal inner bore (not shown) of apparatus 1400 may be positioned appropriately to interact with the transverse bolt through compression slot 1406. Tensioning cable ends (not shown) may pass through support device 1450 and further to tensioning device 1468. Portions of the tensioning cable may be secured to tensioning cable securing cams 1470 of tensioning device 1468. Tensioning cables may be tensioned by twisting ratcheting tension adjustment 1472 to incrementally increase tension of the tensioning cable, and thus the tension between the tensioning cable and transverse bolt through compression slot 1406. As the tensioning cable is tensioned, bones 1440, 1442, and 1444 and their respective joints may be drawn to each other until a desired tensioning has been achieved. Once a desired tensioning is achieved, more transverse bolts may be secured through the drilled apertures on bones 1440, 1442, and 1444 and through apertures corresponding to dynamization slot 1410, and static fixation apertures 1412 of apparatus 1400 to provide a final fixation of apparatus 1400 within bones 1440, 1442, and 1444. After apparatus 1400 has been finally fixated, cams 1470 may be released to slacken the tensioning cable, and tensioning device 1468 may be removed from system 1401. Tensioning cable may be removed from apparatus 1400 via apertures (not shown) on support device 1450. Support device 1450 and its corresponding portion within protective sleeve 1464 may be removed in addition to the nail fastener. Targeting arm 1460 may be removed to leave protective sleeve 1464 as anchored in place. Support rods 1466 may either remain within the body or be removed with protective sleeve 1464. Once protective sleeve 1464 is removed, the soft tissue formerly surrounding 1464 may be closed to complete this example embodiment of a bone compression and fixation procedure.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. An apparatus for use with a tensioning cable and transverse bolts for causing compression between bone elements, the apparatus comprising:
    an elongated shaft having:
        a proximal end, a distal end, and an external surface;
        a longitudinal inner bore;
        a compression slot oriented longitudinally along the shaft and reaching transversely from the external surface to the inner bore, wherein the compression slot is configured to allow longitudinal movement of the shaft relative to a transverse bolt extending through the compression slot into a bone element; and
        a channel extending longitudinally along the inner bore, wherein the entirety of the channel is recessed transversely from the inner bore and is thereby configured to receive a section of a tensioning cable extending within the shaft radially outward of the inner bore.

2. An apparatus as defined in claim 1, wherein the channel is located longitudinally between the compression slot and the proximal end.

3. An apparatus as defined in claim 1, wherein the channel is one of a plurality of channels recessed transversely from the inner bore.

4. An apparatus as defined in claim 3, wherein the channels include channels opposed across the inner bore.

5. An apparatus as defined in claim 1, wherein the shaft further has a cable aperture reaching from the external surface to the inner bore at a location between the compression slot and the proximal end, and the cable aperture is configured to receive a tensioning cable therethrough.

6. An apparatus as defined in claim 5, wherein the channel extends longitudinally from the cable aperture to the compression slot.

7. An apparatus as defined in claim 1, wherein the shaft further has a fixation aperture reaching transversely from the external surface to the inner bore at a location between the compression slot and the proximal end, and wherein the fixation aperture is configured to maintain the shaft in a desired longitudinal position relative to a second transverse bolt extending through the fixation aperture into a second bone element.

8. An apparatus as defined in claim 1, wherein the shaft further has a tensioning cable clearance slot oriented longitudinally along the shaft and reaching transversely from the external surface to the inner bore, wherein the clearance slot is configured to allow a loop of tensioning cable to bow outward from the inner bore through the clearance slot.

9. An apparatus for use with a tensioning cable and transverse bolts for causing compression between bone elements, the apparatus comprising:
    an elongated shaft having:
        a proximal end, a distal end, and an external surface;
        a longitudinal inner bore;
        a compression slot oriented longitudinally along the shaft and reaching transversely from the external surface to the inner bore, wherein the compression slot is configured to allow longitudinal movement of the shaft relative to a transverse bolt extending through the compression slot into a bone element; and
        a channel extending longitudinally along the inner bore, wherein the channel is recessed transversely from the inner bore and is thereby configured to receive a section of a tensioning cable extending within the shaft radially outward of the inner bore;
    wherein the shaft further has a cable aperture reaching from the external surface to the inner bore at a location between the compression slot and the proximal end, and the cable aperture is configured to receive a tensioning cable therethrough; and
    the shaft further has a tensioning cable routing channel reaching along the external surface from the cable aperture toward the distal end.

10. An apparatus as defined in claim 9, wherein the channel is located longitudinally between the compression slot and the proximal end.

11. An apparatus as defined in claim 9, wherein the channel is one of a plurality of channels recessed transversely from the inner bore.

12. An apparatus as defined in claim 11, wherein the channels include channels opposed across the inner bore.

13. An apparatus as defined in claim 9, wherein the channel extends longitudinally from the cable aperture to the compression slot.

14. An apparatus as defined in claim 9, wherein the shaft further has a fixation aperture reaching transversely from the external surface to the inner bore at a location between the compression slot and the proximal end, and wherein the fixation aperture is configured to maintain the shaft in a desired longitudinal position relative to a second transverse bolt extending through the fixation aperture into a second bone element.

15. An apparatus as defined in claim 9, wherein the shaft further has a tensioning cable clearance slot oriented longitudinally along the shaft and reaching transversely from the external surface to the inner bore, wherein the clearance slot is configured to allow a loop of tensioning cable to bow outward from the inner bore through the clearance slot.

16. An apparatus for use with a tensioning cable and transverse bolts for causing compression between bone elements, the apparatus comprising:
    an elongated shaft having:
        a proximal end, a distal end, and an external surface;

a longitudinal inner bore;

a compression slot oriented longitudinally along the shaft and reaching transversely from the external surface to the inner bore, wherein the compression slot is configured to allow longitudinal movement of the shaft relative to a transverse bolt extending through the compression slot into a bone element; and a tensioning cable clearance slot oriented longitudinally along the shaft and reaching transversely from the external surface to the inner bore, wherein the clearance slot is configured to allow a loop of tensioning cable to bow outward from the inner bore through the clearance slot;

wherein the shaft further has a cable aperture reaching from the external surface to the inner bore at a location between the clearance slot and the proximal end, and the cable aperture is configured to receive a tensioning cable therethrough; and the shaft further has a tensioning cable routing channel reaching along the external surface from the cable aperture toward the distal end.

17. An apparatus as defined in claim 16, wherein the clearance slot is one of a plurality of clearance slots, each of which reaches transversely from the external surface to the inner bore and is configured to allow a loop of tensioning cable to bow outward from the inner bore.

18. An apparatus as defined in claim 17, wherein the clearance slots include clearance slots opposed across the inner bore.

19. An apparatus as defined in claim 16, wherein the clearance slot is located longitudinally beside the compression slot.

20. An apparatus as defined in claim 16, wherein the clearance slot is orthogonally offset from the compression slot.

21. An apparatus as defined in claim 16, wherein the shaft further has a channel extending along the inner bore in alignment with the clearance slot, and the channel is recessed transversely from the inner bore to receive a section of a tensioning cable extending within the shaft radially outward of the inner bore.

22. An apparatus as defined in claim 21, wherein the channel is located longitudinally between the compression slot and the proximal end.

23. An apparatus as defined in claim 21, wherein the channel is one of a plurality of channels recessed transversely from the inner bore.

24. An apparatus as defined in claim 23, wherein the channels include channels opposed across the inner bore.

25. An apparatus as defined in claim 16, wherein the shaft further has a fixation aperture reaching transversely from the external surface to the inner bore, wherein the fixation aperture is located between the clearance slot and the proximal end, and is configured to maintain the shaft in a desired longitudinal position relative to a second transverse bolt extending through the aperture into a second bone element.

26. An apparatus for use with a tensioning cable and transverse bolts for causing compression between bone elements, the apparatus comprising:

an elongated shaft having:

a proximal end, a distal end, and an external surface;

a longitudinal inner bore;

a compression slot oriented longitudinally along the shaft and reaching transversely from the external surface to the inner bore, wherein the compression slot is configured to allow longitudinal movement of the shaft relative to a transverse bolt extending through the compression slot into a bone element;

a fixation aperture reaching transversely from the external surface to the inner bore, wherein the fixation aperture is located between the compression slot and the proximal end, and is configured to maintain the shaft in a desired longitudinal position relative to a second transverse bolt extending through the aperture into a second bone element;

a cable aperture reaching through the shaft from the external surface to the inner bore at a location between the compression slot and the proximal end, wherein the cable aperture is configured to receive a tensioning cable therethrough; and a channel extending along the inner bore, wherein the channel is recessed transversely from the inner bore to receive a section of a tensioning cable extending within the shaft radially outward of the inner bore;

wherein the channel extends longitudinally from the cable aperture to the compression slot; and the shaft further has a tensioning cable routing channel reaching along the external surface from the cable aperture toward the distal end.

27. An apparatus as defined in claim 26, wherein the channel is located longitudinally between the compression slot and the proximal end.

28. An apparatus as defined in claim 26, wherein the channel is one of a plurality of channels recessed transversely from the inner bore.

29. An apparatus as defined in claim 28, wherein the channels include channels opposed across the inner bore.

30. An apparatus as defined in claim 26, wherein the shaft further has a tensioning cable clearance slot oriented longitudinally along the shaft and reaching transversely from the external surface to the inner bore, wherein the clearance slot is configured to allow a loop of tensioning cable to bow outward from the inner bore through the clearance slot.

* * * * *